United States Patent
Carchidi et al.

[11] Patent Number: 5,971,985
[45] Date of Patent: Oct. 26, 1999

[54] BONE ATTACHMENT DEVICE FOR USE WITH TISSUE GRAFTS AND MEMBRANES

[75] Inventors: Joseph E. Carchidi, West Bridgewater, Mass.; Alan R. Balfour, Camarillo, Calif.

[73] Assignee: ACE Surgical Supply Co., Inc., Brockton, Mass.

[21] Appl. No.: 08/928,944

[22] Filed: Sep. 12, 1997

[51] Int. Cl.[6] .................................................. A61B 77/56
[52] U.S. Cl. ............................... 606/61; 606/72; 606/73; 606/53; 606/65; 606/66
[58] Field of Search ................................. 606/61, 72, 73, 606/53, 65, 66

[56] References Cited

U.S. PATENT DOCUMENTS

| | | | |
|---|---|---|---|
| 2,382,019 | 8/1945 | Miller | 606/72 |
| 2,685,877 | 8/1954 | Dobelle | 606/72 |
| 2,853,913 | 9/1958 | Rapata | 156/73.5 |
| 3,466,966 | 9/1969 | Brown | 411/510 |
| 3,494,244 | 2/1970 | Wayland | 411/510 |
| 3,810,279 | 5/1974 | Swick et al. | 411/509 |
| 4,402,641 | 9/1983 | Arff | 411/510 |
| 4,551,189 | 11/1985 | Peterson | 411/508 |
| 4,976,715 | 12/1990 | Bays et al. | 606/77 |
| 5,261,914 | 11/1993 | Warren | 606/72 |

*Primary Examiner*—Michael Buiz
*Assistant Examiner*—Tan-Uyen Thi Ho
*Attorney, Agent, or Firm*—John A. Haug

[57] ABSTRACT

A self-locking and threaded bone tack screw device (10) for fixing and retaining tissue grafts and synthetic membranes directly to a maxillofacial bone graft site. The tack has an oversized cylindrical dome shaped head (14) for retaining the tissue and synthetic membrane to the bone graft site and a hexagonal recess (14a) for easy insertion and removal of the device. The tip of the device incorporates a sharp pin point (12a) to easily pierce the tissue and membrane and initially penetrate into the bone graft site. A locking flange (12c) locks into the bone graft site in a single direction. A self-tapping screw thread (12f) is provided for driving the pin point tip into the bone graft site. Incorporation of the self-locking pin point tip in series with the self-tapping thread allows the hexagonal tool driven bone tack to be easily inserted and removed from the graft site without compromising its fixation.

9 Claims, 3 Drawing Sheets

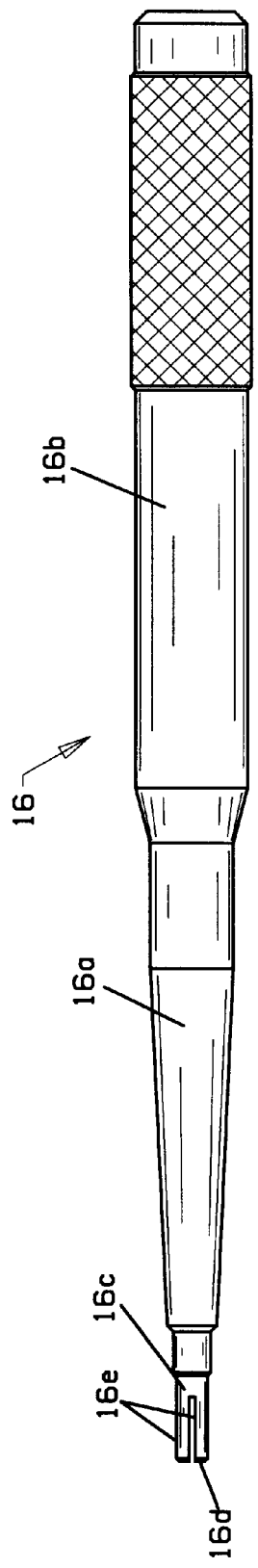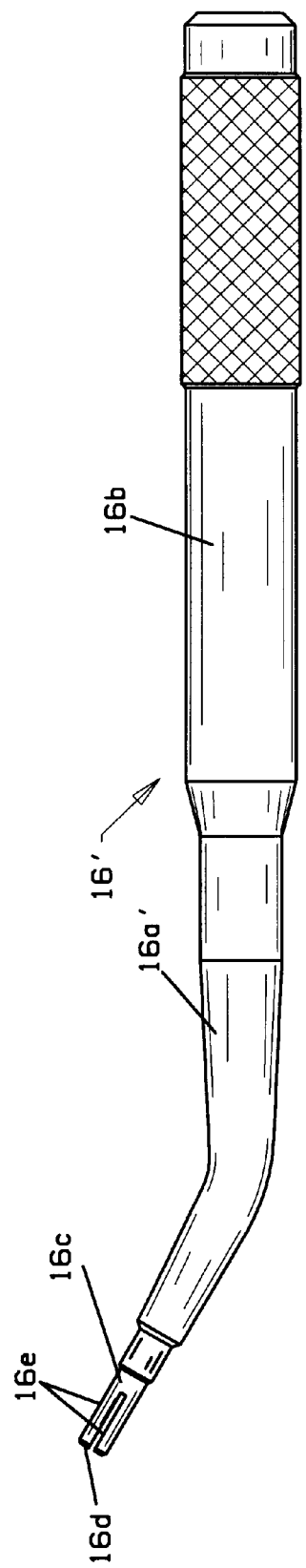

BONE ATTACHMENT DEVICE FOR USE WITH TISSUE GRAFTS AND MEMBRANES

FIELD OF THE INVENTION

This invention relates generally to surgical devices and more particularly to surgical fixation and retention devices used in grafting tissue and synthetic membrane to a maxillofacial bone graft site.

BACKGROUND OF THE INVENTION

Presently two types of fixation devices are used for the retention of tissue grafts and synthetic membranes to a maxillofacial bone graft site, namely, a standard threaded bone screw and a simple pin point tack.

The threaded bone screw type incorporates a defined self-tapping thread to thread through the tissue or synthetic graft material before screwing into the bone graft site. Threading this self-tapping screw through the tissue or synthetic membrane and into the bone graft site, however, requires a certain degree of skill as the thread can easily engage and tear the tissue or synthetic membrane during insertion. Additionally, it involves a challenge to locate, stabilize and self-start the bone screw into the desired graft site and in most cases requires a surgical pilot hole.

To overcome the functional deficiencies of the bone screw design and to simplify surgical requirements, a push pin tack was developed. The push pin tack design incorporates a pin point tip that easily penetrates through the tissue or membrane graft and drives a cylindrical shaft directly into the bone site. This push pin bone tack provides a quick and easy surgical alternative for fixing tissues or synthetic membranes to a graft site. However, without the rigid fixation provided by the screw design, one takes the risk of a separation from the graft during the healing phase.

SUMMARY OF THE INVENTION

An object of the present invention is to provide an improved bone attachment device to rigidly retain a tissue or synthetic membrane to a maxillofacial bone graft site. Another object of the invention is to provide a bone attachment device that quickly and easily pierces the tissue or synthetic device without catching thereon and starts into the bone graft device. Yet another object is the provision of a device which overcomes the limitations of the prior art noted above.

Briefly stated, in accordance with the invention, a tissue and synthetic membrane bone attaching device comprises a self-tapping bone tack screw that incorporates a sharp unidirectional pin point in series with a self-tapping threaded bone screw body. Distal to the tip and body of the bone tack is a cylindrical dome shaped head that can be inserted or removed using a hexagonal screw driving tool. The invention solves the problems of locating, stabilizing and self-starting the bone screw tack into the graft site without compromising the fixation functional requirements. The novel device provides the doctor with a cost effective, easy to use, functional alternative for fixing tissue or synthetic membranes to a maxillofacial bone graft site. According to the invention, the device forms a pilot hole in the bone graft site by a pin point portion which then facilitates driving of a self-tapping threaded body into the preformed pilot hole thereby allowing the doctor to quickly and easily insert the device into the bone graft site without compromising the fixation of the graft.

Additional objects and features of the invention will be set forth in part in the description which follows and in part will be obvious from the description. The objects and advantages of the invention may be realized by means of the instrumentalities and combinations particularly pointed out in the appended claims.

BRIEF DESCRIPTION OF THE DRAWINGS

The accompanying drawings, which are incorporated in and constitute a part of the specification, illustrate a preferred embodiment of the invention and, together with the description, serve to explain the objects, advantages and principles of the invention. In the drawings:

FIGS. 2 and 3 are views, partly broken away, of delivery and drive tools for the FIG. 1 bone Attachment device.

DETAILED DESCRIPTION OF THE PREFERRED EMBODIMENT

Figure 1:
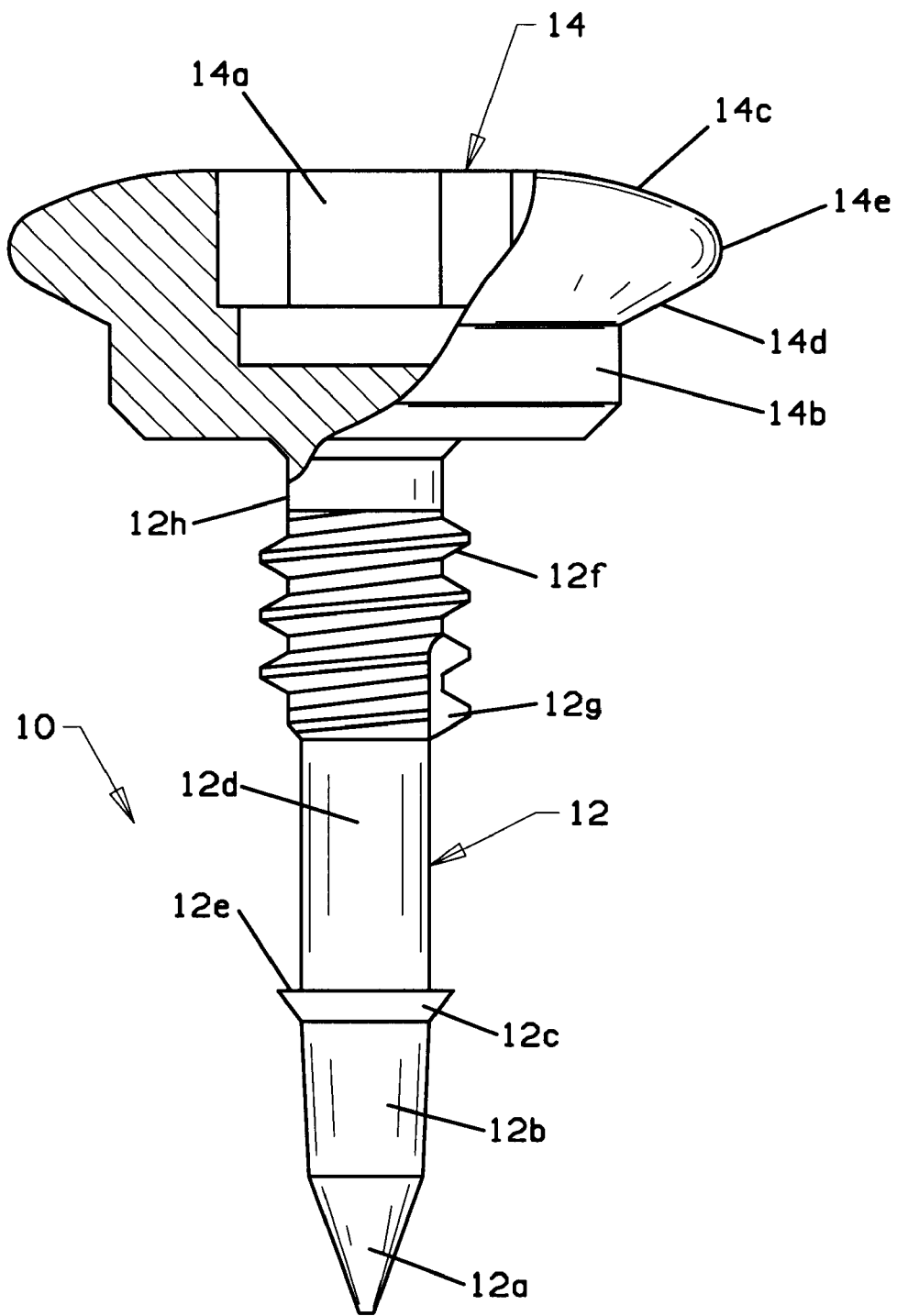
FIG. 1 is an enlarged view, partly in cross-section, of a bone attachment device made in accordance with the invention.

As shown in FIG. 1, the bone attachment device 10, made in accordance with the invention, comprises a cylindrical, self-tapping pin point tack body 12 and a cylindrical dome shaped driving head 14. Body 12 is adapted to locate, stabilize and self-start into the bone graft site with minimal effort while achieving maximum fixation. To achieve this result, body 12 incorporates a sharp pin point 12a extending over a first axial length portion to a first diameter to easily pierce into the graft site. The diameter of the cylindrical body progressively, relatively gradually increases from the pin point along a second axial length portion 12b to a second diameter and a tapered, circumferentially extending, locking flange 12c. The diameter of locking flange 12c increases relatively rapidly as one continues along a third axial length in the direction from the pin point tip 12a toward head 14 and then the diameter steps back to a reduced fourth diameter cylindrical shaft portion 12d forming a radially extending locking surface 12e to lock into the bone graft site in a single direction. The reduced diameter fourth axial length portion of cylindrical shaft portion 12d, distal to locking flange 12c, serves to remove any resistance for the shaft portion 12d in penetrating into the graft site. Finally, to achieve maximum fixation, bone attachment device 10 incorporates in an additional axial length portion a self-tapping thread 12f with a lead-in cutting flute 12g for easy insertion into or removal from the graft site. As shown in FIG. 1, an axial length portion 12h is provided between thread 12f and head 14 for thread relief.

The coronal end of bone attachment device 10 incorporates an oversized cylindrical dome shaped driving head 14 for retention of a tissue graft or synthetic membrane. Dome shaped driving head preferably has a diameter approximately five times that of the fourth diameter portion. Located in the center of the cylindrical dome-shaped driving head is a standard hexagonal recess 14a for driving the tack in or out of the bone graft site. The underside portion of the cylindrical dome shaped driving head has a reduced diameter or step portion 14b for seating the graft material at a selected distance from the dome shaped radii at 14c, 14d. Step portion 14b minimizes the risk of bone growing over the dome shaped head 14 during the healing phase and causing any additional surgical procedures.

Bone attachment device 10 may be provided in different lengths by varying the axial length of shaft portion 12d. By way of example in devices made in accordance with the invention, for a long bone screw tack having a total axial length of 0.202 inch, shaft portion 12d has a length of 0.083 inch and for a short bone screw having a total axial length of 0.124 inch, shaft portion 12d has a length of 0.005 inch. Otherwise the dimensions of the several portions remain the same in both versions. For example, step portion 14b may have a diameter of 0.070 inch, head 14 may have a diameter of approximately 0.0985/0.0975 and fourth axial length portion 12d may have a diameter of 0.019/0.017 inch.

Figure 4:
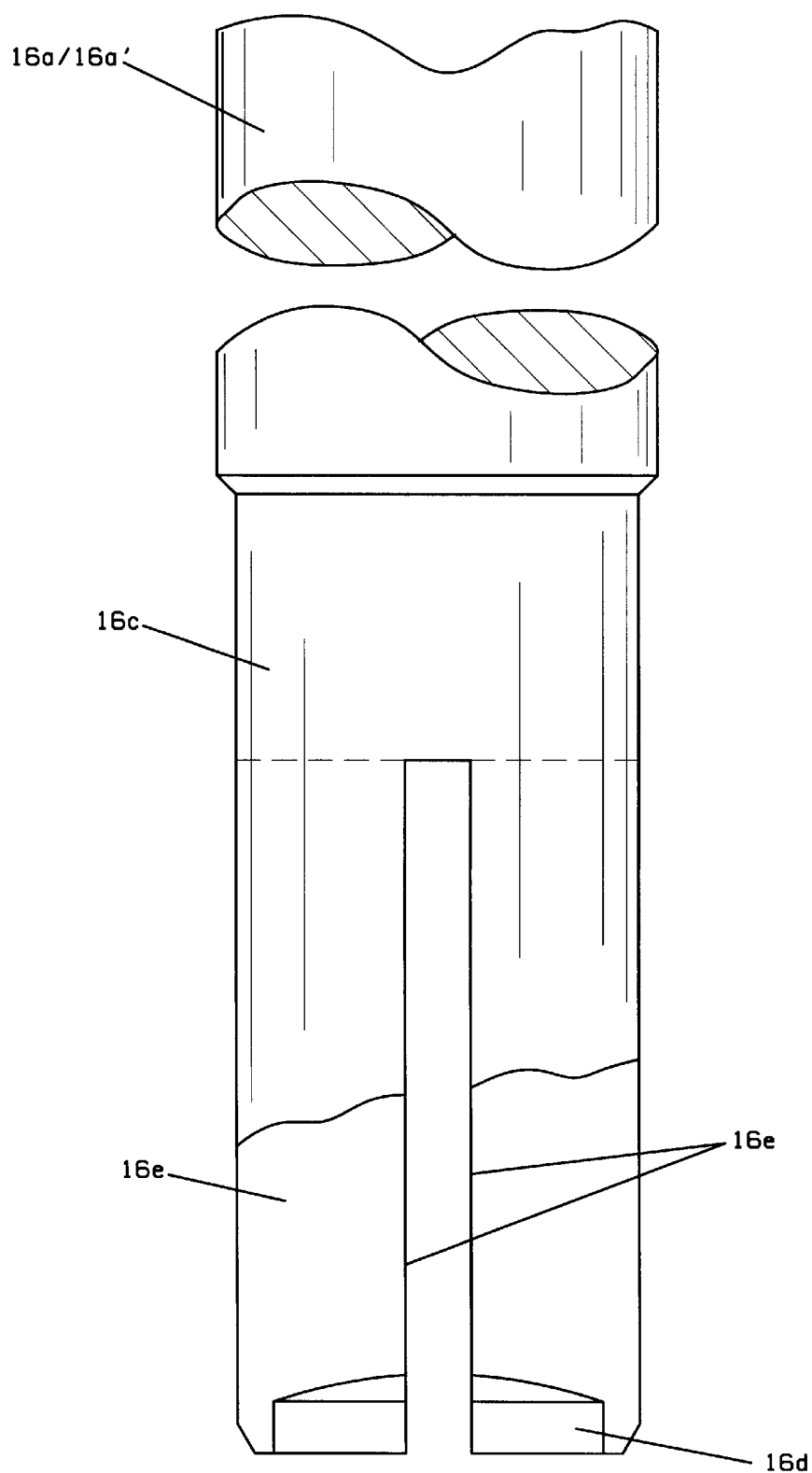
FIG. 4 is an enlarged view of a portion of the FIGS. 2 and 3 tools.

With reference to FIGS. 2–4, a press-fit pick-up and delivery tool 16 of FIG. 2 or 16' of FIG. 3 may be used to deliver device 10 to a graft site. The tool securely snaps over the intersecting diameter 14e of the two cylindrical dome shaped surface portions 14c and 14d of the driving head. Tools 16, 16' are made up of a threaded detachable delivery head 16a, 16a' (see FIG. 3) and a knurled driver handle 16b. Tip 16c of the delivery head has an essentially identical or complimentary female geometry 16d to that of driving head 14 for press-fitting thereon. Four slits 16e are incorporated into the tip of the delivery head to snap over driving head 14 of the bone attachment device and deliver the device to the graft site with minimal effort. The frictional snap retention of driving head 14 of bone attachment device 10 into the female geometry 16d can be used to initiate the seating of the bone attachment device 10. Final seating of the device can be completed using a standard hexagon driver, such as a 0.9 mm hexagon driver. To further assist the doctor in areas that are difficult to access, the straight delivery head 16a can be unthreaded from the driver handle 16b and replaced with an angled delivery head 16a'. Angled delivery head 16a' is used to press-fit over and deliver the bone attachment device 10 to areas having difficult accessibility in the same manner as the straight delivery head 16a.

In use, bone attachment device 10 is carried and delivered to the bone graft site by either of tools 16, 16' and then is tapped into the bore with the locking flange 12c serving to retain the device securely in the bore formed by tip 12a and portion 12b. The tool then can be rotated so that the threads begin to engage the bone defining the bore. Once the device is sufficiently engaged, the tool can be snapped off head 14 and further insertion and removal can be accomplished by means of a conventional hexagonal screw driver.

Although the invention has been described with respect to a specific preferred embodiment thereof, variations and modifications will become apparent to those skilled in the art. It is, therefore, the intention that the appended claims be interpreted as broadly as possible in view of the prior art to include all such variations and modifications.

What is claimed:

1. An attachment device for retaining tissue and synthetic membranes to a bone graft site comprising:

an elongated cylindrical body member extending along a longitudinal axis from a first end to a second, opposite end with reference to a selected direction taken along the longitudinal axis, the first end formed with a pin point tapering up to a first diameter forming a first axial length portion, a second axial length portion extending from the first axial length portion and increasing in diameter at a given angle with respect to the selected direction to a second diameter, a third axial length portion forming a tapered locking flange increasing diameter at a greater angle with respect to the selected direction then the given angle, the locking flange extending from the second diameter to a third diameter having a third axial length and having a locking surface extending around the periphery generally perpendicular to the longitudinal axis at the third diameter extending radially inwardly to a fourth axial length portion having a fourth diameter extending from the third axial length portion and an additional axial length portion having a self-tapping thread and a relatively enlarged tissue and membrane retaining head formed at the second end, the head having a step portion having a selected diameter greater than the fourth diameter and less than the diameter of the head and having a selected axial length to inhibit bone growth over the head.

2. An attachment device according to claim 1 in which the screw thread includes a cutting flute along a portion of the axial length of the thread.

3. An attachment device according to claim 1 in which the head has an axial length of approximately 0.036/0.034 inch.

4. An attachment device according to claim 1 in which the head has a diameter approximately five times the fourth diameter of the fourth axial length portion.

5. An attachment device according to claim 1 in which the head has a non-circular, tool receiving recess formed therein.

6. An attachment device according to claim 1 in which the overall length is between approximately 0.124 and 0.202 inch and the diameter of the head is approximately 0.0985/0.0975 inch, the diameter of the step portion is 0.070 inch and the axial length of the head is approximately 0.036/0.034 inch, the fourth diameter of the fourth axial length portion is approximately 0.019/0.017 inch.

7. An attachment device according to claim 6 in which the fourth axial length is between approximately 0.005 and 0.083 inch.

8. An attachment device according to claim 1 in which an axial length of a selected amount is formed between the additional axial length portion and the head for thread relief.

9. An attachment device for retaining tissue and synthetic membranes to a bone graft site comprising:

an elongated cylindrical body member extending along a longitudinal axis from a first end to a second, opposite end with reference to a selected direction taken along the longitudinal axis, the first end formed with a pin point tapering up to a first diameter forming a first axial length portion, a second axial length portion extending from the first axial length portion, a tapered locking flange diameter with respect to the first direction extending from a second diameter at the second axial length portion to a third diameter defining a third axial length portion and having a locking surface generally perpendicular to the longitudinal axis at the third diameter extending generally radially inwardly to a fourth axial length portion having a fourth diameter, an additional axial length portion extending from the fourth axial length portion having a self-tapping thread and a relatively enlarged tissue and membrane retaining head formed at the second end, the head having a diameter approximately five times larger than the fourth diameter, and the head having a step portion having a selected diameter greater than the fourth diameter and less than the diameter of the head and having a selected axial length to inhibit bone growth over the head.

* * * * *